United States Patent
Bacchi et al.

[11] Patent Number: 6,023,630
[45] Date of Patent: Feb. 8, 2000

[54] PROBE ASSEMBLY AND APPARATUS FOR MEASURING THE PH OF A TISSUE OF A HUMAN OR ANIMAL ORGAN

[75] Inventors: Bernard Bacchi, Garches; Patrick Marchot, Quincy; Philippe Mauriat, Vanves; Philippe Pouard, Clamart; Gilles Touati, Amiens Cedex; Alain Magnard, Longpont Sur Orge, all of France; Fernard Muller, Vianden, Luxembourg

[73] Assignee: Electrolux S.A.R.L., Vianden, Luxembourg

[21] Appl. No.: 08/799,567

[22] Filed: Feb. 12, 1997

[30] Foreign Application Priority Data

Feb. 12, 1996 [FR] France .................................. 96 01699

[51] Int. Cl.[7] ......................................................... A61N 5/00
[52] U.S. Cl. ........................................... 600/348; 600/345
[58] Field of Search ..................................... 600/345–350, 600/361–365; 178/897–898

[56] References Cited

U.S. PATENT DOCUMENTS

| | | | |
|---|---|---|---|
| 4,301,807 | 11/1981 | Mentelos | 128/635 |
| 4,384,586 | 5/1983 | Christiansen | 600/361 |
| 4,440,620 | 4/1984 | Ono et al. | 600/361 |
| 4,568,444 | 2/1986 | Nakamura et al. | 600/361 |
| 4,579,641 | 4/1986 | Shimomura et al. | 600/361 |
| 4,618,929 | 10/1986 | Miller et al. | 600/348 |
| 4,641,249 | 2/1987 | Glon et al. | 600/345 |
| 4,700,709 | 10/1987 | Kraig | 600/345 |
| 4,734,184 | 3/1988 | Burleigh et al. | 600/361 |
| 4,935,345 | 6/1990 | Guikbeau et al. | 600/345 |
| 5,051,352 | 9/1991 | Martindale et al. | 435/1 |
| 5,147,524 | 9/1992 | Broadley | 600/361 |
| 5,338,435 | 8/1994 | Betts et al. | 600/361 |
| 5,354,448 | 10/1994 | Markle et al. | 600/348 |
| 5,507,289 | 4/1996 | Essen-Moller | 600/348 |
| 5,680,858 | 10/1997 | Hansen et al. | 600/345 |

FOREIGN PATENT DOCUMENTS 4216412  12/1992  Germany.

OTHER PUBLICATIONS

International Journal of Electronics, vol. 56, No. 4, Apr. 1984, pp. 443–456, M.A. Stuchly, et al.: Permittivity of Mammalian tissues in vivo and in Vitro; Advances in Experimental Techniques and Recent Results.

Primary Examiner—Cary O'Connor
Assistant Examiner—Michael Astorino
Attorney, Agent, or Firm—Oblon, Spivak, McClelland, Maier & Neustadt, P.C.

[57] ABSTRACT

A probe assembly includes at least two electrodes for measuring a potential difference between two measurement sites of a tissue of a human or animal organ and at least one sensor for measuring the tissue temperature. The probe assembly further includes a common support on which are placed the electrodes and the sensor. The support comprises conductors for linking the electrodes and the sensor to a signal processing unit with a view to calculating the tissue pH of the organ.

6 Claims, 1 Drawing Sheet

PROBE ASSEMBLY AND APPARATUS FOR MEASURING THE PH OF A TISSUE OF A HUMAN OR ANIMAL ORGAN

BACKGROUND OF THE INVENTION

Field of the Invention

The present invention relates to a probe assembly intended for measuring the pH of a human or animal organ as well as to an apparatus for measuring pH including such a probe assembly.

DISCUSSION OF THE BACKGROUND

Probe assemblies of this type are commonly used in the fields of medicine and experimentation and in particular to check the state of a live organ, such as a heart, a liver, a kidney, etc.

The technique of organ transplantation calls upon a donor from which an organ or a group of organs is removed and upon a recipient onto which the organ thus removed is grafted in order to replace a defective organ which has previously undergone ablation.

It is not very common for the donor and the recipient to be simultaneously close in time and in space. It is therefore necessary to preserve and usually to transport the organ between its place of removal and its place of reimplantation.

After removal of an organ from a donor and in the course of its transport, it is necessary to check the state of preservation of the organ.

This checking is carried out for example by means of the continuous checking of the intracellular pH, which reflects for the heart for example, the quality of the myocardial cells.

To do this, two measurement electrodes are sunk into the removed organ at corresponding measurement sites with a view to measuring the potential difference between these sites. Furthermore, the temperature of the organ is monitored, likewise continuously, by sinking a temperature sensor into it.

These electrodes and this sensor are linked to a processing unit providing for the calculation of the pH on the basis of the measured values of the potential difference and temperature.

This type of operation exhibits numerous drawbacks, especially by reason of the fact that it is necessary to insert the electrodes and the sensor into the organ during monitoring, thereby causing impairment of the constituent tissue of the organ, and that the placing of the electrodes and of the sensor is a relatively lengthy and tricky operation.

SUMMARY OF THE INVENTION

The purpose of the invention is to alleviate these drawbacks.

Therefore, an object of the present invention is to provide for a probe assembly of the aforementioned type which includes a common support on which are placed the electrodes and the sensor. The support comprises conductors for linking the electrodes and the sensor to a signal processing unit with a view to calculating the tissue pH of the organ.

The invention can furthermore include one or more of the following features:

the measurement electrodes include a measurement electrode proper in the form of a needle intended to be sunk into the tissue of the organ and a metal reference electrode in the form of a plate intended to be applied to the surface of the tissue, with a view to measuring a potential difference between an internal measurement site and an external measurement site;

the reference electrode is covered with a porous substance which can deform elastically in accordance with the shape of the tissue of the organ and is soaked with an electrically conducting fluid;

the sensor for measuring the tissue temperature is a contact measurement sensor intended to be applied to the external surface of the organ;

the common support includes a printed circuit board on one face of which are fixed the electrodes and the sensor at corresponding connection sites; and the printed circuit board is covered with a flexible insulating substance extending laterally via a rim for suturing the board to the organ.

A further object of the present invention is to provide for an apparatus for measuring the pH of a tissue of a human or animal organ which includes a probe assembly such as defined above, linked to a signal processing unit in which is stored an algorithm for calculating the pH of the organ from values of the potential difference and from the temperature which are delivered respectively by the electrodes and the sensor.

The present invention therefore provides for a probe assembly which comprises first and second electrodes for measuring a potential difference between two corresponding measurements sites of tissue of a human or animal organ; at least one sensor for measuring a tissue temperature; and a common support on which are placed the first and second electrodes and the at least one sensor. The common support comprises conductors for linking the first and second electrodes and the at least one sensor to a signal processing unit with a view to calculating a tissue pH of the organ.

The present invention also provides for an apparatus for measuring a pH of a tissue of a human or animal organ. The apparatus comprises a probe assembly including first and second electrodes for measuring a potential difference between two corresponding measurement sites of the tissue of a human or animal organ; and at least one sensor for measuring a tissue temperature. The probe assembly includes a common support on which are placed the first and second electrodes and the at least one sensor. The common support comprises conductors for linking the first and second electrodes and the at least one sensor to a signal processing unit with a view to calculating the tissue pH of the organ. The probe assembly is linked to a signal processing unit in which is stored an algorithm for calculating the pH of the organ from values of the potential difference and from the temperature which are delivered respectively by the first and second electrodes in the sensor.

The present invention also provides for a probe assembly which comprises measuring means for measuring a potential difference between designated positions on a tissue of a human or animal organ; sensing means for measuring a tissue temperature; and supporting means for supporting the measuring means and the sensing means. The supporting means comprising linking means for linking the measuring means and the sensing means to a processing means for calculating a tissue pH of the organ.

BRIEF DESCRIPTION OF THE DRAWINGS

In describing the preferred embodiments of the present invention illustrated in the drawings, specified terminology is employed for the sake of clarity. However, the invention is not intended to be limited to the specific terminology so selected, and it is to be understood that each specific element includes technical equivalents which can operate for a similar purpose.

A more complete appreciation of the invention and many of the attendant advantages thereof will be readily determined as the same becomes better understood by references to the following detailed description when considered in connection with the accompanying drawings, wherein.

DESCRIPTION OF THE PREFERRED EMBODIMENTS

Figure 1:
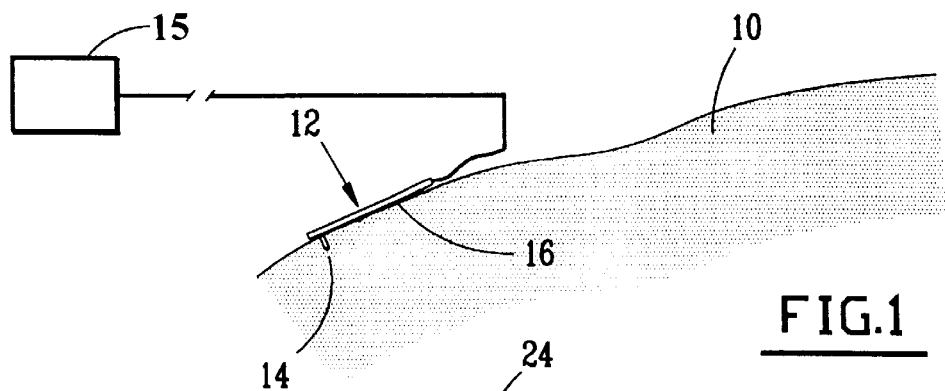
FIG. 1 is a schematic view of an apparatus for measuring the pH of the tissue of a human or animal organ.

Referring now the to drawings, wherein like reference numerals designate identical or corresponding parts throughout the several views, represented in FIG. 1 is an apparatus for measuring the pH of the myocardial tissue of a heart 10.

This measurement apparatus comprises a probe assembly 12 linked to a signal processing unit 15.

The probe assembly 12, which will be described in detail with reference to FIGS. 2 to 4, measures a potential difference between two measurement sites 14 and 16 of the heart 10, as well as the temperature of the latter.

The probe assembly 12 delivers the measurement values of the potential difference and of the temperature to the processing unit 15 in which is stored a conventional algorithm for calculating the pH of the heart 10 from the measured values of the potential difference and of the temperature of the organ.

Figure 2:
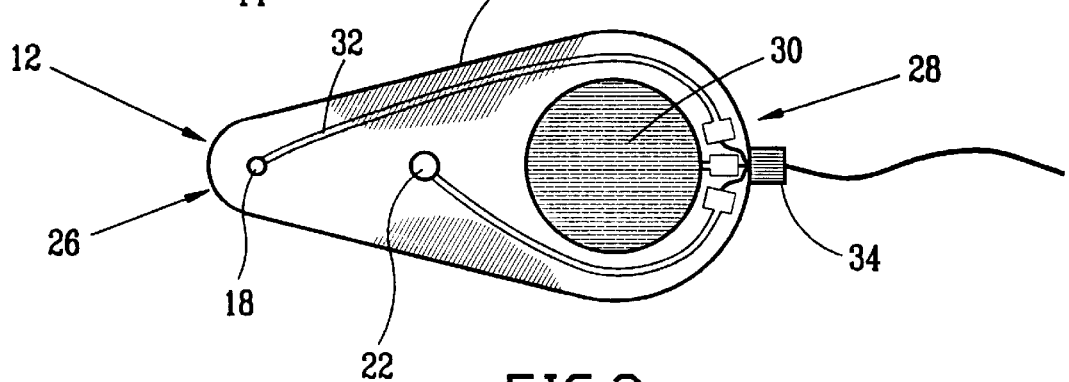
FIG. 2 is a bottom view of a probe assembly according to the invention.
Figure 3:
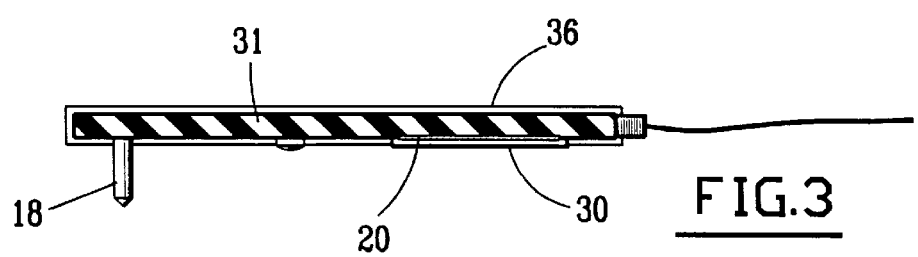
FIG. 3 is a longitudinal section view of the probe assembly of FIG. 2.

Referring to FIGS. 2 and 3, it may be seen that the probe assembly 12 includes two electrodes 18 and 20 for measuring the potential difference between the two measurement sites 14 and 16 (FIG. 1) and a sensor 22 for measuring the temperature of the organ. The measurement electrodes 18 and 20 as well as the sensor 22 are fixed on one face of a common support 24 made from an insulating material.

The support 24 preferably has the shape of an ovoid plate on the lower face of which are fixed the electrodes 18 and 20 and the sensor 22.

The measurement electrodes 18 and 20 comprise the electrode 18 which can be a measurement electrode proper in the form of a needle running perpendicular to the overall plane of the support 24, in the vicinity of its smaller end region 26, and the electrode 20 which can be a reference electrode that includes a metal plate fixed on the support 24 in the vicinity of its larger end region 28.

It may be seen in particular in FIG. 3 that the reference electrode 20 is advantageously covered with a foam 30 made from a porous substance which can deform elastically so as to adapt to the morphology of the organ 10. The porous substance can include any non-toxic known substance compatible with human or animal organ tissues. It is soaked with an electrically conducting jelly of conventional type, providing for an electrical link between the reference electrode 20 and the organ 10.

The temperature sensor 22 includes a contact measurement sensor fixed on that face of the support 24 on which the measurement electrodes 18 and 20 are fixed.

As mentioned earlier, the support 24 comprises a plate of ovoid shape. The plate 24 has a composite structure.

The plate 24 includes a core 31 made from a rigid material such as a rigid plastic or a resin, on which there runs a set of conductors, such as 32, linking the measurement electrodes 18 and 20 and the measurement sensor 22 to a terminal 34 for the electrical connection of the probe assembly 12 to the signal processing unit 15.

It is therefore appreciated that the plate 24 thus constitutes a printed circuit board on which the electrodes 18 and 20 and the temperature sensor 22 are fixed at corresponding connection sites.

Referring in particular to FIG. 3, it may be seen that the core 31 is covered with an insulating envelope 36, made for example of araldite, providing for the protection of the conductors 32 as well as for their electrical insulation.

The apparatus of the present invention operates as follows:

After removal of the organ 10, the support 24 is positioned manually on the surface of the organ 10 and the measurement electrode 18 is sunk into it.

It is appreciated that with the end region 26 on which the measurement electrode 18 is fixed having a relatively small surface area, the measurement site into which this measurement electrode 18 will be sunk can be easily viewable, thereby avoiding the perforation of surface vessels of the organ 10.

In this position, in which the measurement electrode 18 is sunk into the organ 10, the reference electrode 20 and the temperature sensor 22 are applied against the surface of the organ.

Thus, the probe assembly 12, as soon as it is connected up to the central processing unit 15, sends the latter measurement values of the difference in internal and external potential between the two-measurement sites 14 and 16 as well as the value of the surface temperature of the organ 10.

The signal processing unit 15 provides for the calculation of the pH by using these measurement values delivered by the probe assembly 12, on the basis of a calculational algorithm of known type stored in the processing unit 15. It is thus possible continuously to monitor the variation in the intracellular pH of the organ 10 with a view to monitoring its state of preservation.

Figure 4:
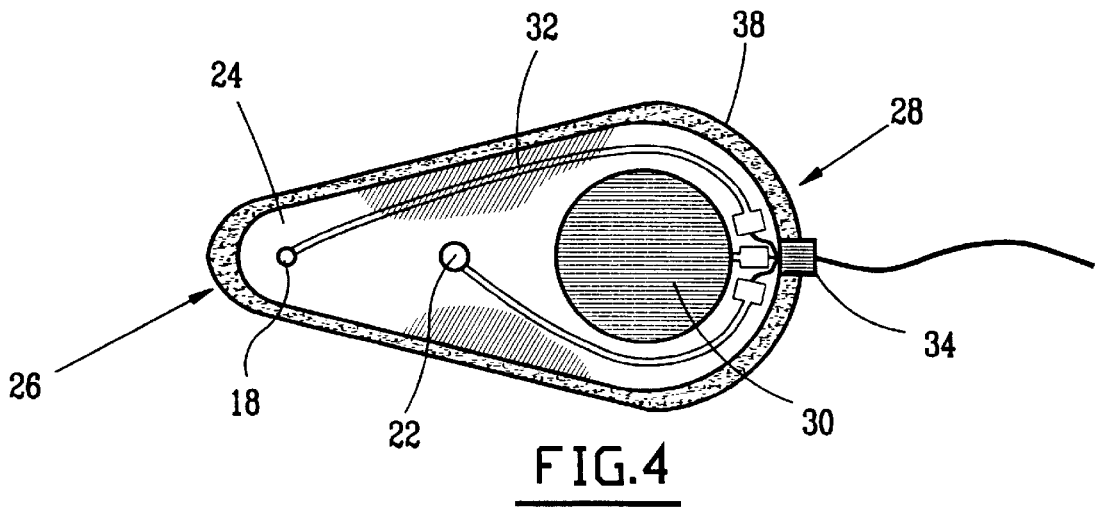
FIG. 4 is a bottom view of the probe assembly according to another embodiment.

According to another embodiment represented in FIG. 4, the support 24 is covered with a flexible substance, made for example of fabric, extending laterally via a rim 38 intended for the suturing of the probe assembly to the organ with a view to its mechanical fixing.

This flexible insulating substance comprises a non-toxic fabric compatible with organ tissues, for example "GOR-TEX".

In the example represented in FIG. 4, the upper face, opposite to the face on which the electrodes and the sensor are fixed, is covered with fabric, but of course both faces of the support 24 may be covered with this flexible substance.

Obviously, numerous modifications and variations of the present invention are possible in light of the above teachings. It is therefore to be understood that within the scope of the appended claims, the invention may be practiced otherwise than as specifically described herein.

What is claimed as new and is desired to be secured by Letters Patent of the United States is:

1. A probe assembly comprising:

first and second electrodes for measuring a potential difference, comprising a measurement electrode in the form of a needle intended to be sunk into tissue and a metal reference electrode in the form of a plate intended to be applied to a surface of the tissue for calculating a potential difference between an internal measurement site and an external measurement site;

at least one sensor for measuring the tissue temperature; and a common support on which are placed the electrodes and the sensor and comprising conductors for linking the electrodes and the sensor to a signal processing unit to calculate the tissue pH.

2. A probe assembly according to claim 1, wherein said metal reference electrode is covered with a porous substance which can deform elastically in accordance with a shape of the tissue of an organ and is soaked with an electrically conducting fluid.

3. A probe assembly according to claim 1, wherein said at least one sensor for measuring the tissue temperature is a contact measurement sensor intended to be applied to an external surface of an organ.

4. A probe assembly according to claim 1, wherein said common support includes a printed circuit board on one face of which are fixed said first and second electrodes and said at least one sensor at corresponding connection sites.

5. A probe assembly according to claim 4, wherein said printed circuit board is covered with a flexible insulating substance extending laterally via a rim for suturing said printed circuit board to said organ.

6. An apparatus for measuring a pH of a tissue of a human or animal organ, the apparatus comprising:

a probe assembly including first and second electrodes for measuring a potential difference between two corresponding measurement sites of the tissue of a human or animal organ; and at least one sensor for measuring a tissue temperature;

wherein the probe assembly includes a common support on which are placed said first and second electrodes and said at least one sensor, said common support comprising conductors for linking the first and second electrodes and the at least one sensor to a signal processing unit for calculating the tissue pH of the organ, said probe assembly being linked to a signal processing unit in which is stored an algorithm for calculating the pH of the organ from values of the potential difference and from the temperature which are delivered respectively by said first and second electrodes and said sensor.

* * * * *